United States Patent [19]

Aldred et al.

[11] 4,421,583

[45] Dec. 20, 1983

[54] MAN-MADE FILAMENTS AND METHOD OF MAKING WOUND DRESSINGS CONTAINING THEM

[75] Inventors: Fred C. Aldred, Cumbria; Charles R. Moseley, Coventry, both of England

[73] Assignee: Courtaulds Limited, London, England

[21] Appl. No.: 421,231

[22] Filed: Sep. 22, 1982

Related U.S. Application Data

[63] Continuation of Ser. No. 220,042, Dec. 18, 1980, abandoned.

[30] Foreign Application Priority Data

Apr. 18, 1979 [GB] United Kingdom ................ 7913392

[51] Int. Cl.³ .............................................. D04H 3/16
[52] U.S. Cl. .................................... 156/167; 8/115.5;
128/156; 156/181; 156/229; 156/281; 156/285;
156/306.3; 156/308.8; 162/187; 162/206;
162/207; 162/157.1; 264/103; 264/178 F
[58] Field of Search .............. 156/181, 285, 161, 296,
156/167, 306.3, 229, 308.8, 281; 162/187, 207,
206, 217, 157 R; 264/103, 178 F; 8/130.1,
115.5; 128/156; 428/198, 296, 288, 392; 28/100,
134, 122; 536/3; 424/28

[56] References Cited

U.S. PATENT DOCUMENTS

| 2,142,722 | 1/1939 | Dreyfus et al. ......................... 8/132 |
| 2,496,797 | 2/1950 | Kenyon et al. ......................... 536/3 |
| 2,512,616 | 6/1950 | Eberl et al. ........................... 128/156 |
| 2,600,504 | 6/1952 | Johnson et al. ................. 162/157 R |
| 3,293,116 | 12/1966 | Opderbeck et al. ............ 162/157 R |
| 3,531,363 | 9/1970 | Shambelan ........................... 428/198 |
| 3,621,531 | 11/1971 | Fertgen et al. ....................... 28/100 |
| 3,802,980 | 4/1974 | Harmon ............................... 156/181 |
| 4,104,115 | 8/1978 | Prouse et al. .................... 162/157 R |

FOREIGN PATENT DOCUMENTS

| 21586 | of 1913 | United Kingdom ................ 8/115.5 |
| 1231506 | 5/1971 | United Kingdom .................... 536/3 |
| 1287885 | 9/1972 | United Kingdom ................ 156/181 |

*Primary Examiner*—John J. Gallagher
*Attorney, Agent, or Firm*—Howson and Howson

[57] ABSTRACT

A non-woven alginate fabric useful as a wound dressing is made by spreading a tow of calcium alginate filaments in a flow of water, overfeeding the spread filaments onto a water-pervious support so that the filaments cross over each other and drying the filaments so that the alginate filaments become bonded to each other at their points of contact where they cross over each other. The filaments used have preferably been stretched in an atmosphere of steam and water-washed but not dried and are preferably dried by suction on the water-pervious support.

5 Claims, 2 Drawing Figures

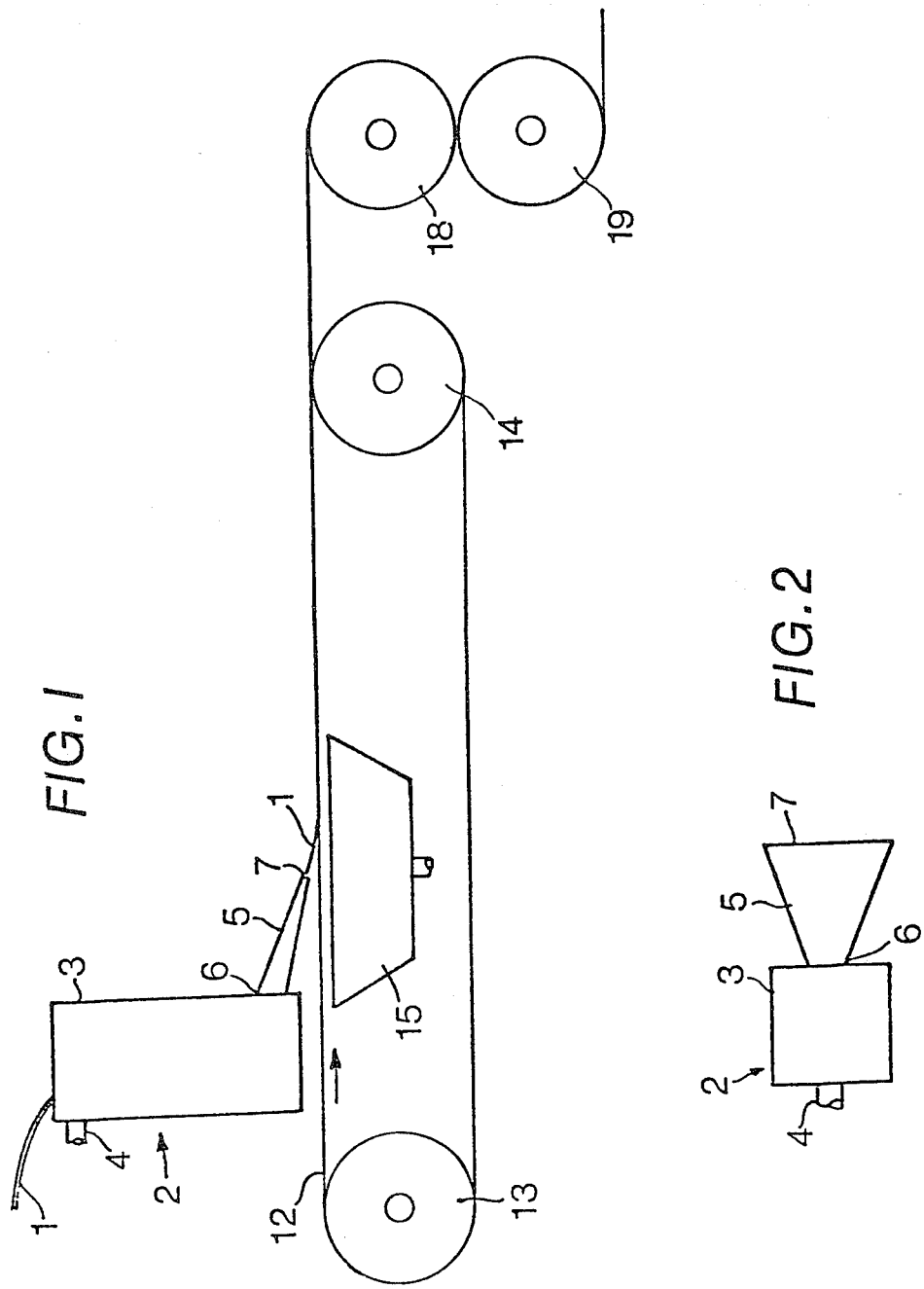

4,421,583

MAN-MADE FILAMENTS AND METHOD OF MAKING WOUND DRESSINGS CONTAINING THEM

This application is a continuation of application Ser. No. 220,042, filed Dec. 18, 1980, (now abandoned).

TECHNICAL FIELD

This invention relates to alginate filaments and to wound dressings containing them.

BACKGROUND ART

The extrusion of alginate solutions into an aqueous solution containing calcium ions to form yarns of calcium alginate filaments is known, for example, from British Pat. Nos. 567,641, 568,177, 571,657 and 624,987. The alginate yarn when formed into a fabric is useful as a haemostatic wound dressing as described in British Pat. No. 621,320. Such fabrics have generally been prepared by knitting a yarn of calcium alginate filaments and partially converting the calcium alginate to the sodium form to form a calcium sodium alginate containing, for example, 30–70 percent by weight of the carboxy groups of the alginate in the calcium form. This process is difficult in practice. The alginate fibres in the calcium form are brittle and in the sodium calcium alginate form they are very weak and sensitive to moisture.

DISCLOSURE OF INVENTION

A process according to the invention for making a nonwoven alginate fabric useful as a wound dressing comprises spreading a tow of calcium alginate filaments in a flow of water, overfeeding the spread filaments onto a water-pervious support so that the filaments cross over each other and drying the filaments so that the filaments become bonded to each other at their points of contact where they cross over each other.

The calcium alginate filaments can be prepared by extruding a 5 to 10 percent aqueous solution of sodium alginate into an aqueous solution containing 5 to 35 grams/liter of calcium chloride or an equivalent amount of any other calcium salt. The sodium alginate solution can be treated with an oxidising agent such as hydrogen peroxide, chlorine or sodium hypochlorite (e.g. in an amount of 1–10 percent by weight, based on sodium alginate) to reduce its viscosity and is then preferably filtered before extrusion to form filaments. The extruded tow preferably comprises 4000 to 40,000 filaments of total decitex 10,000–100,000. The freshly spun calcium alginate tow is preferably stretched, suitably by a factor of 1.5 to 2.5, in an atmosphere of steam, preferably at 90°–120° C., while still wet with calcium salt solution. Steam stretching, particularly when following oxidation of the alginate solution, leads to stronger, more lustrous and less brittle filaments. It also reduces the water content of the filaments, which when freshly spun are in a swollen gel state. The steam stretched filaments are particularly suitable for forming a non-woven fabric according to the invention. Hot-stretching has not previously been used in calcium alginate filaments because of the risk of filament breakage during stretching. The oxidation of the alginate solution before extrusion leads to fibres strong enough to survive stretching.

The tow is preferably spread by feeding a tow of calcium alginate filaments, which have been stretched and water-washed but not dried, through a fish tail device whose cross-section gradually widens in a first direction and narrows in a second direction at right angles to the first.

The degree of overfeeding of the spread filaments on to the water-pervious support is preferably at least 2 percent, that is to say the speed of the filaments is preferably at least 2 percent greater than the speed of the support, for example a wire mesh conveyor, on which they are laid. The degree of overfeeding can be as high as 200 percent or even more. However, we prefer an overfeed of 10–50 percent which we have found gives a substantially uniform layer of filaments with sufficient crossing over of filaments to lead to a unitary non-woven fabric when the filaments are bonded.

The web of calcium alginate filaments formed on the support is preferably dried by first sucking surplus water from beneath the water-pervious support so as to bond the filaments together at their points of contact and finally by heating, for example by passing over cylinders heated to 120°–150° C., to remove all residual water.

The calcium alginate filaments, particularly if they have been spun into solutions containing 5–10 grams/liter $CaCl_2$, and have been subjected to hot stretching, have a ribbon-like cross-section and have a natural tendency to bond together on drying, like paper fibres. This cross-section is also responsible in part for the greatly reduced brittleness of the fibres. The dried web produced is thus a stable non-woven fabric in which the filaments are bonded at their points of contact where they cross over each other. The degree of bonding of the filaments can be increased by treating the filaments while they are on the conveyor with an aqueous solution of a sodium salt, to replace part of the calcium ions by sodium ions to form calcium sodium alginate fibres. The sodium salt is preferably a salt of an acid which forms an insoluble calcium salt, for example the carbonate, sulphite, oxalate or palmitate. The sodium salt solution can be applied as a spray.

The freshly spun and stretched calcium alginate filaments spread in the flow of water generally contain about 95 percent of their carboxyl groups in the calcium form and 5 percent in the sodium form. Treatment with a sodium salt solution to increase the bonding of the filaments on the conveyor slightly increases their sodium content, but the calcium content should generally remain above 70 percent. Non-woven alginate fabrics having this high calcium content of 70 to 95 percent are useful for example as throat swabs, which after swabbing are dissolved in sodium hexametaphosphate solution. The non-woven alginate fabrics can be treated to partially replace calcium by sodium, for example by treatment with alcoholic sodium hydroxide and sodium acetate so that from 30 to 70 percent of the carboxyl groups are in the sodium form. The sodium calcium alginate fabrics produced are useful as haemostatic wound dressings which can be absorbed by body fluids, for use for example in deep surgery or after tooth extraction.

BRIEF DESCRIPTION OF DRAWING

The invention will now be described by way of example, with reference to the accompanying drawing, in which:

FIG. 1 is a diagrammatic side elevation of an apparatus for forming non-woven fabric of alginate filaments according to the invention, and FIG. 2 is a top view of the spreading device used in the apparatus of FIG. 1.

BEST MODE OF CARRYING OUT THE INVENTION

Referring to the drawing, to produce a non-woven fabric according to the invention a tow 1 of stretched and washed calcium alginate filaments is fed to a spreading device 2. The spreading device consists of a chamber 3 containing water continuously fed in through an inlet 4 and a fish tail device 5 which forms the outlet of the spreading device. The fish tail is of substantially square cross-section at the point 6 where it joins with chamber 3, but its outlet 7 is in the form of a broad slit.

A water-pervious support 12, for example a wire mesh conveyor, passes under fish tail 5 and around rolls 13 and 14 in the direction shown. The spread tow of alginate filaments emerging from the fish tail 5 is led on the mesh conveyor as the tow passes from the outlet 7 of the fish tail. The speed of the alginate filaments emerging from the outlet 7 is arranged to be greater, for example 20 percent greater than the speed of the conveyor 12. The water carrying the alginate filaments passes through the conveyor 12 to a receptacle 15 under the upper flight of the conveyor. Suction is applied to the filaments on the belt through the receptacle 15; alternatively or additionally, a separate suction box can be mounted beneath the conveyor and further along the conveyor.

The web of partially dried calcium alginate filaments parts from the conveyor at roll 14 and passes around heated cylinders 18 and 19 which further dry the alginate filaments.

The invention is illustrated by the following Example.

EXAMPLE 600 g of sodium alginate were dissolved with a high-speed stirrer in 10 liters of cold water containing 18 g chlorine in the form of sodium hypochlorite. After standing for 16 hours, enough sodium sulphite was added to just prevent a reaction to starch iodide paper. The solution was then filtered and spun through a stainless steel jet having 40,000 75$\mu$ holes, into 0.8 weight percent $CaCl_2$ solution. Calcium alginate filaments formed in the solution. The freshly-spun filaments were then stretched by a factor of 2.0 in an atmosphere of steam at a temperature of 100° C. and then washed with fresh water.

The stretched calcium alginate tow was fed to the apparatus shown in FIGS. 1 and 2, the speed of the conveyor 12 being such as to give a 20 percent overfeed of the tow. The spread filaments were laid in a sinuous configuration with the filaments crossing over one another and drying by suction while the filaments were on the conveyor 12 bonded the filaments in this configuration to produce a non-woven alginate fabric which was dried by heated cylinders 18 and 19.

We claim:

1. A process for making a non-woven alginate fabric useful as a wound dressing comprising forming a tow of continuous calcium alginate filaments by extruding an alginate solution which has been treated with an oxidising agent into an aqueous solution of a calcium salt, stretching the tow of continuous calcium alginate filaments while still wet with calcium salt solution in an atmosphere of steam, spreading in a flow of water the tow of stretched continuous calcium alginate filaments which have been water washed but not dried, overfeeding the spread filaments onto a water pervious support so that the filaments cross over each other, and drying the filaments by suction while they are on the water-pervious support to such extent that the filaments become self-bonded to each other at their points of contact where they cross over each other in the absence of an adhesive or heat.

2. A process according to claim 1 in which the tow is spread by feeding it through a device whose cross-section gradually widens in a first direction and narrows in a second direction at right angles to the first.

3. A process according to claim 1 or claim 2 in which the degree of overfeeding of the spread filaments is 10 to 50 percent.

4. A process according to claim 1 or claim 2, wherein the filaments are treated on the support with an aqueous solution of a sodium salt to replace part of the calcium ions by sodium ions, more than 70 percent of the carboxyl groups remaining in the calcium form.

5. A process according to claim 1 or claim 2, wherein the finished fabric is treated to partially replace calcium with sodium, from 30 to 70 percent of the carboxyl groups remaining in the calcium form.

* * * * *